United States Patent [19]

Stewen

[11] Patent Number: 5,298,641

[45] Date of Patent: Mar. 29, 1994

[54] METHOD OF PREPARING DISTANNANES

[75] Inventor: Ulrich Stewen, Schwerte, Fed. Rep. of Germany

[73] Assignee: Witco GmbH, Bergkamen, Fed. Rep. of Germany

[21] Appl. No.: 85,509

[22] Filed: Jun. 30, 1993

[30] Foreign Application Priority Data

Sep. 17, 1992 [DE] Fed. Rep. of Germany ....... 4231083

[51] Int. Cl.$^5$ ................................................. C07F 7/22
[52] U.S. Cl. ......................................... 556/82; 556/87
[58] Field of Search .................................. 556/82, 87

[56] References Cited

U.S. PATENT DOCUMENTS

| | | | |
|---|---|---|---|
| 3,211,769 | 10/1965 | Brown et al. | 260/429.7 |
| 3,442,197 | 1/1969 | Molt et al. | 424/283 |
| 3,652,618 | 3/1972 | Reifenberg et al. | 260/429.7 |
| 3,699,138 | 10/1972 | Debreczeni et al. | 260/429.7 |
| 3,726,906 | 4/1973 | Reifenberg et al. | 260/429.7 |

OTHER PUBLICATIONS

Houben Weyl, Methoden der Organischen Chemie Band vol. 13/6, pp. 401–416 (1978).
A. G. Davies, P. J. Smith, Comprehensive Organometallic Chemistry, Pergamon Press, 591 (1982).
A. K. Sawyer: Organotin Compounds vol. 3, Marcel Dekker, Inc. New York 1972, 823–879.
W. P. Neumann, Die Organische Chemie des Zinns, Ferdinand Enke Verlag, Stuttgart 1967, 102–121.
W. P. Neumann, B. Schneider, Angew. Chem., Int. Ed. Engl. 3, 751, (1964).
W. P. Neumann, J. Pedain, Tetrahedron Lett. No. 36, pp. 2461–2465 (1964).
W. P. Neumann, Angew. Chem. 73, 541 (1961).
CA 98:89536y Synthesis of hexaalkyl- and hexaaryldistannanes from $R_3SnH$ in the presence of palladium complexes. Bunagin et al. Izv. Akad. Nauk SSSR Ser. Khim. 1982 (11).
CA 101: 11072 y Synthesis of hexaalkyl(aryl)distannanes and their reactions with organic halides under catalysis conditions by palladium complexes Bumagin, et al. Izv. Akad. Nauk sSSR, Ser. Khim. 1984 (5), 1137–42.
B. Jousseaume et al., J. Organomet. Chem., 294 (3), C41–45 (1985).
G. Wittig et al., Liebigs Ann. Chem. 571, 167 (1951).
B. Jousseaume, E. Chanson, M. Pereyre, Organometallics, 5 (6), 1271-2 (1986).
CA 72:90593j Preparation of hexaalkytditin and reaction with aroyl chloride. Shirai, et al. Yakugaku Zasshi, 1970, 90(1), 59–63.
R. K. Ingham, S. D. Rosenberg und H. Gilmann, Chem. Rev. 60, 459 (1960).
G. Grüttner, Chem. Ber. 1917, 50, 1808.

*Primary Examiner*—José G. Dees
*Assistant Examiner*—Porfirio Nazario-Gonzalez
*Attorney, Agent, or Firm*—Scully, Scott, Murphy & Presser

[57] ABSTRACT

The present invention relates to a method of preparing hexaalkyl distannanes by converting bis-[trialkyltin]oxide with a stabilized solution of sodium borohydride in alcohol, preferably methanol, in the presence of an inert solvent.

15 Claims, No Drawings

METHOD OF PREPARING DISTANNANES

FIELD OF THE INVENTION

The present invention relates to an improved method of preparing hexaalkyl distannanes of the general formula $R_1R_2R_3Sn-SnR_1R_2R_3$ wherein $R_1$, $R_2$, and $R_3$ are the same or different, branched or unbranched, and/or substituted alkyls having from 1 to 18 carbon atoms by a simple processing procedure which results in a substantial to near quantitative yield of the distannane.

BACKGROUND OF THE INVENTION

Hexaalkyl distannanes, especially hexabutyl distannanes, are valuable and extraordinarily versatile reagents for organic synthesis. As catalysts, the hexaalkyl distannanes are attracting increasing interest in a number of different technical processes.

Detailed information can be obtained from several reviews, including: W. P. Neumann, *Die Organische Chemie des Zinns*, Stuttgart, Ferdinand Enke Verlag, 1967; R. C. Poller, *The Chemistry of Organotin Compounds*, Logos Press Ltd., 1970; M. Pereyre, J. P. Quintard, and A. Rahm, *Tin in Organic Synthesis*, London, Butterworth, 1987; I. Omar, *Organotin Chemistry*, Amsterdam, Elsevier, 1989; and P. G. Harrison, *Chemistry of Tin*, Glasgow, Blackie.

Various methods of preparing distannanes have been described in the prior art. However, these prior art methods are oftentimes very complicated to run, have low yields, or require such costly starting materials such as trialkyltin hydrides, which makes them unattractive for industrial applications. Thus, continued research is ongoing to develop a simple and more cost-effective method of preparing distannanes, a few of these methods are described hereinbelow.

The preparation of compounds which contain tin-to-tin bonds is described in numerous publications such as: Houben Weyl, *Methoden der Organischen Chemie*, Vol. 13,6 401–16; A. G. Davies and P. J. Smith, *Comprehensive Organometallic Chemistry*, Pergamon Press, 591; A. K. Sawyer, *Organotin Compounds*, Vol. 3, New York, Marcel Dekker, Inc., 1972, 823–79; and W. P. Neumann, *Die Organische Chemie des Zinns*, Stuttgart, Ferdinand Enke Verlag, 1967.

The condensation of trialkyltin hydrides with trialkyltin amines and alkoxides or with bis-[trialkyltin] oxides produces satisfactory yields of hexaalkyl distannanes. However, this reaction requires expensive starting materials and is difficult to handle due to the high reactivity of the starting compounds. This condensation reaction is described in W. P. Neumann & B. Schneider, *Angew. Chem.*, Int. Ed. Engl., 3, 751 (1964) and W. P. Neumann & J. Pedain, *Tetrahedron Lett.*, Int. (1964), 2461.

W. P. Neumann, *Angew. Chem.* 73, 541 (1961) discloses a method of producing high yields of hexaalkyl distannanes from trialkyltin hydrides by catalytically removing the hydrogen therefrom.

Chemical Abstract Nos. 98:89536 y and 101:111072 y describe the synthesis of distannanes from the corresponding hydrides in the presence of a palladium complex. Yields of 71 to 89% are obtained from this process. More specifically, the trialkyltin hydrides are produced in-situ by reducing the trialkyltin or triaryltin chlorides with lithium aluminum hydride.

B. Jousseaume, et al., *J. Organomet. Chem*, 294 (3), C41–45, discloses a process for converting bis-[trialkyltin] oxide with formic acid. However, this method produces hexaalkyl distannane which are contaminated with poly-tin compounds.

German Application No. 1 955 241 discloses a method of preparing hexaalkyl distannanes from trialkyltin formiates by thermolysis. The product obtained by this method is extensively contaminated with various decomposition side products.

Chemical Abstract No. 95:123026 g (Japanese A 56 058 981) describes a method for preparing distannanes through the complicated electrolysis of trialkyltin and triaryltin formiates.

The conversion of trialkyltin lithium or sodium with trialkyltin halides into distannanes is described by G. Wittig, et al. in *Liebigs Ann. Chem.*, 571, 167 (1961).

U.S. Pat. No. 3,699,138 describes the preparation of distannanes from trialkyltin halides with molten sodium.

B. Jousseaume, E. Chanson, Mr. Pereyre, *Organometallics*, 5 (b), 1271–724 discloses a method of reducing bis-[trialkyltin]oxide with titanium, potassium, sodium, or magnesium which subsequently results in yields of about 60 to 82% of hexaalkyl distannanes.

Chemical Abstract No. 72:90593 j provides a method of converting tributyltin chloride with magnesium in tetrahydrofuran which results in yields of about 70% of hexabutyl distannanes.

Hexaalkyl distannanes can also be prepared by a Wurtz reaction from trialkyltin halides and metallic sodium in liquid ammonia or ether. This reaction is described, for example, in R. K. Ingham, S. D. Rosenberg, and H. Gilmann, *Chem. Rev.*, 60, 459 (1960) and G. Grüttner, *Chem. Ber.*, 1917, 50, 1808.

BE A 672 867 disclosed the conversion of sodium in tetrabutyltin with tributyltin chloride followed by a complicated process which yields 93% of hexabutyl distannane.

Despite the current state of the art, none of the references disclosed hereinabove describes the current method of preparing hexaalkyl distannanes.

SUMMARY OF THE INVENTION

It has surprisingly, now been discovered that hexaalkyl distannanes of general formula $R_1R_2R_3Sn-SnR_1R_2R_3$ wherein $R_1$, $R_2$, and $R_3$ are same or different, branched or unbranched, and/or substituted alkyls having from 1 to 18 carbon atoms can be prepared by a simple and reliable procedure. More specifically, the present invention provides a method of preparing hexaalkyl distannanes, by converting bis-[trialkyltin]oxide with a stabilized solution of sodium borohydride ($NaBH_4$) in the presence of an inert solvent.

DETAILED DISCUSSION OF THE PRESENT INVENTION

In accordance with the inventive method, hexaalkyl distannanes of the general formula $R_1R_2R_3Sn-SnR_1R_2R_3$ wherein $R_1$, $R_2$, and $R_3$ are the same or different, branched or unbranched, and/or substituted alkyls having from 1 to 18 carbons can be prepared by converting bis-[trialkyltin]oxide with a stabilized solution of sodium borohydride in an alcohol in the presence of an inert solvent.

This reaction described hereinabove is allowed to proceed for about ½ to about 3 hours after the initial reflux period at a temperature of about 0° to about 200° C. More preferably, the reaction is carried out at a temperature of about 50° to about 80° C.

Suitable alcohols that are employed by the present invention as a reaction medium include aliphatic or aromatic alcohols containing from about 1 to about 12 carbon atoms. In a preferred embodiment of the present invention, the alcohol is an aliphatic alcohol containing from 1 to 5 carbon atoms. Of these preferred alcohols, methanol is especially preferred.

It is a preferred embodiment of the present invention that the inert solvent does not react with either the hexaalkyl distannanes or the intermediately produced organotin hydrides, or the sodium borohydride. Examples of suitable inert solvents that satisfy this criterion are ethyl ether, dioxane, acetonitrile, and hydrocarbons. Tetrahydrofuran is most particularly preferred.

In accordance with another embodiment of the present invention, the starting compounds are preferably added stoichiometrically in the range of about 0.5 to about 1.5 moles of sodium borohydride per mole of bis-[trialkyltin]oxide.

The invention procedure is rendered more reliable by using a stabilized solution of sodium borohydride in a reaction medium comprising an alcohol. Bases such as sodium hydroxide are particularly appropriate as stabilizers which can be added to the sodium borohydride solution.

The conversion of the bis-[trialkyltin]oxide can be further accelerated by adding about 0.1 to about 10% by weight of hydrogen-acid compounds therein. Suitable hydrogen-acid compounds employed by the present invention include thiosalicylic acid, lactic acid, 1-dodecanethiol, and thioglycolic acid. Of these compounds, thioglycolic acid is most particularly preferred.

In contrast to previously known methods, the reaction of the present invention is simple and more reliable. Furthermore, the starting materials employed herein are easier to handle and more cost-effective than prior art materials. Thus, the distannanes produced by the present invention may be used in a wide variety of industrial applications, such as catalysts.

The conversion of bis-[trialkyltin]oxides into hexaalkyl distannanes with a stabilized solution of sodium borohydride in alcohol is easy to regulate by controlling the addition of reductant. Furthermore the reversed addition can also be carried out no loss of product.

Without wishing to be bound by any mechanism, the intermediate trialkyltin hydride is formed probably from the reaction of the sodium borohydride with the bis-[trialkyltin]oxide, while the components are being added, and immediately converts into the hexaalkyl distannane.

A high-purity hexaalkyl distannane is then isolated subsequent to distilling the solvent off and filtration.

The particular advantage of the present method is the simplicity of the reaction, which allows an almost quantitative yield of the desirable hexaalkyl distannanes in a one-pot procedure using inexpensive and easy to handle starting materials.

The following examples are given to illustrate the scope of the present invention. Because these examples are given for illustrative purposes only, the invention embodied therein should not be limited thereto.

EXAMPLES

Example 1

8.5 g (0.22 moles) of sodium borohydride dissolved in 200 ml of methanol and stabilized with 8.0 g (0.2 moles) of sodium hydroxide are added over the course of 1 hour at the reflux temperature to a solution of 119.2 g (0.2 moles) of bis-[tributyltin]oxide in 100 ml of tetrahydrofuran.

The reaction was allowed to proceed for another hour at the reflux temperature and then cooled. The tetrahydrofuran was then separated out. It should be noted that the overall yield can be further increased by extracting the methanol with tetrahydrofuran. Thereafter the tetrahydrofuran was distilled out. Filtration resulted in the isolation of 111 g (96%) of hexabutyl distannane that chromatography reveals to be more than 96% pure. The product contained neither tributyltin hydride nor bis-[tributyltin]oxide.

Example 2

119.2 g (0.2 moles) of bis-[tributyltin]oxide dissolved in 100 ml of tetrahydrofuran are added over the course of 1 hour at reflux temperature to a solution of 8.5 g (0.22 moles) of sodium borohydride in 100 ml of methanol stabilized with 8.0 g (0.2 moles) of sodium hydroxide.

The reaction was allowed to proceed for another hour at reflux temperature. The solvent was then distilled off and the product was recovered by filtering out the precipitated solids. The yield was 109 g (94%) of hexabutyl distannane.

Example 3

The conversion of bis-[tributyltin]oxide was carried out using the conditions described in Example 1, however, 1.5% thioglycolic acid by weight was added thereto. This resulted in a 97% yield of the distannane with no side-products.

Example 4

8.5 g (0.2 moles) of sodium borohydride dissolved in 200 ml of ethanol and stabilized with 8.0 g (0.2 moles) of sodium hydroxide are added over the course of 1 hour at the reflux temperature to a solution of 119.2 g of bis-[tributyltin]oxide in 100 ml of tetrahydrofuran.

The reaction was allowed to proceed for another hour at the reflux temperature Thereafter, the solvent was distilled off. The product was then filtered out of precipitated solids. A yield of 104 g (90%) of hexabutyl distannane was isolated.

Example 5

8.5 g (0.22 moles) of sodium borohydride dissolved in 200 ml of methanol and stabilized with 8.0 g of sodium hydroxide are added over the course of 1 hour at reflux temperature to a solution of 186.5 g (0.2 moles) of bis-[trioctyltin]oxide in 150 ml of tetrahydrofuran. The processing described with reference to Example 1 resulted in the isolation of 176 g (96%) hexaoctyl distannane.

The above embodiments and examples are given to illustrate the scope and spirit of the present invention. These embodiments and examples will make apparent, to those skilled in the art, other embodiments and examples. These other embodiments and examples are within the contemplation of the present invention; therefore, the instant invention should be limited only by the appended claims.

What is claimed is:

1. A method of preparing hexaalkyl distannanes of general formula $$R_1R_2R_3Sn\text{---}SnR_1R_2R_3$$

wherein $R_1$, $R_2$, and $R_3$ are the same or different and are branched or unbranched alkyls having from 1 to 18 carbon atoms, characterized by converting bis-[trialkyltin]oxide with a stabilized solution of sodium borohydride in alcohol in the presence of an inert solvent.

2. The method of claim 1 wherein the alcohol is an aliphatic or aromatic alcohol containing from 1 to 12 carbon atoms.

3. The method of claim 2 wherein the alcohol is an aliphatic alcohol containing from 1 to 5 carbon atoms.

4. The method of claim 3 wherein the aliphatic alcohol is methanol.

5. The method of claim 1 wherein the reaction is allowed to proceed for about ½ to 3 hours.

6. The method of claim 1 wherein the inert solvent does not react with either the hexaalkyl distannanes, or the intermediately produced organotin hydrides, or the sodium borohydride.

7. The method of claim 6 wherein the inert solvent is tetrahydrofuran.

8. The method of claim 1 wherein the molar ratio of bis-[trialkyltin]oxide to sodium borohydride is approximately 1:1.

9. The method of claim 1 wherein the solution of sodium borohydride in an alcohol is stabilized with a base.

10. The method of claim 9 wherein the base is sodium hydroxide.

11. The method of claim 1 wherein the reaction is further accelerated by added about 0.1 to about 10% by weight of hydrogen-acid compounds thereto.

12. The method of claim 11 wherein the hydrogen-acid compounds are thiosalicylic acid, lactic acid, 1-dodecanethiol or thioglycolic acid.

13. The method of claim 12 wherein the hydrogen-acid compound is thioglycolic acid.

14. The method of claim 1 wherein the conversion occurs at a temperature of about 0° to about 200° C.

15. The method of claim 14 wherein the temperature is from about 50° to about 80° C.

* * * * *

UNITED STATES PATENT AND TRADEMARK OFFICE
CERTIFICATE OF CORRECTION

PATENT NO. : 5,298,641
DATED : March 29, 1994
INVENTOR(S) : Ulrich Stewen

It is certified that error appears in the above-indentified patent and that said Letters Patent is hereby corrected as shown below:

```
       Column 2, line 15:   "(1961)"   should read
--(1951)--
```

Signed and Sealed this

Sixth Day of December, 1994

Attest:

BRUCE LEHMAN

Attesting Officer

Commissioner of Patents and Trademarks